(12) United States Patent
Sun et al.

(10) Patent No.: US 8,804,116 B2
(45) Date of Patent: *Aug. 12, 2014

(54) SURFACE-ENHANCED RAMAN SCATTERING SUBSTRATE AND RAMAN DETECTING SYSTEM HAVING THE SAME

(75) Inventors: Ying-Hui Sun, Beijing (CN); Kai Liu, Beijing (CN); Kai-Li Jiang, Beijing (CN); Jiao Miao, Beijing (CN); Shou-Shan Fan, Beijing (CN)

(73) Assignees: Tsinghua University, Beijing (CN); Hon Hai Precision Industry Co., Ltd., New Taipei (TW)

( * ) Notice: Subject to any disclaimer, the term of this patent is extended or adjusted under 35 U.S.C. 154(b) by 353 days.

This patent is subject to a terminal disclaimer.

(21) Appl. No.: 12/815,551

(22) Filed: Jun. 15, 2010

(65) Prior Publication Data

US 2011/0063613 A1 Mar. 17, 2011

(30) Foreign Application Priority Data

Sep. 15, 2009 (CN) .......................... 2009 1 0190213

(51) Int. Cl.
*G01N 21/65* (2006.01)
*B82Y 15/00* (2011.01)
*B82Y 40/00* (2011.01)

(52) U.S. Cl.
CPC ............... *G01N 21/658* (2013.01); *B82Y 15/00* (2013.01); *B82Y 40/00* (2013.01)
USPC ........................................ 356/301

(58) Field of Classification Search
CPC ................................................. G01N 21/658

USPC .......................................................... 356/301
See application file for complete search history.

(56) References Cited

U.S. PATENT DOCUMENTS

| 5,818,047 | A | 10/1998 | Chaney et al. | |
|---|---|---|---|---|
| 6,713,519 | B2 * | 3/2004 | Wang et al. | 518/715 |
| 7,242,470 | B2 * | 7/2007 | Cullum et al. | 356/301 |
| 7,351,588 | B2 * | 4/2008 | Poponin | 436/171 |
| 7,397,558 | B2 * | 7/2008 | Kamins et al. | 356/301 |
| 7,466,406 | B2 * | 12/2008 | Mirkin et al. | 356/301 |
| 7,486,400 | B2 * | 2/2009 | Saito | 356/445 |

(Continued)

FOREIGN PATENT DOCUMENTS

| CN | 1957245 | 5/2007 |
|---|---|---|
| CN | 101239712 | 8/2008 |

(Continued)

OTHER PUBLICATIONS

Sun et al. ("Highly Sensitive Surface-Enhanced Raman Scattering Substrate Made from Superaligned Carbon Nanotubes"); NanoLetters 2010, 10, 1747-1753, published on web Apr. 13, 2010.*

(Continued)

*Primary Examiner* — Gregory J Toatley
*Assistant Examiner* — Rufus Phillips
(74) *Attorney, Agent, or Firm* — Novak Druce Connolly Bove + Quigg LLP

(57) ABSTRACT

A surface-enhanced Raman scattering substrate includes a carbon nanotube film structure and a plurality of metallic particles disposed on the carbon nanotube film structure. The carbon nanotube film structure includes a number of carbon nanotubes joined by van der Waals attractive force therebetween. The carbon nanotube film structure is a free-standing structure.

15 Claims, 17 Drawing Sheets

(56) References Cited

U.S. PATENT DOCUMENTS

| | | | |
|---|---|---|---|
| 2003/0218744 A1* | 11/2003 | Shalaev et al. | 356/301 |
| 2005/0084980 A1* | 4/2005 | Koo et al. | 436/171 |
| 2007/0153269 A1 | 7/2007 | Wang et al. | |
| 2008/0248235 A1 | 10/2008 | Feng et al. | |
| 2008/0286526 A1* | 11/2008 | Konakahara | 428/137 |
| 2009/0068448 A1 | 3/2009 | Liu et al. | |
| 2009/0155467 A1 | 6/2009 | Wang et al. | |
| 2009/0197082 A1 | 8/2009 | Jiang et al. | |
| 2009/0201496 A1 | 8/2009 | Lee et al. | |
| 2009/0224435 A1 | 9/2009 | Gogotsi et al. | |
| 2010/0062226 A1 | 3/2010 | Hulteen et al. | |
| 2010/0233472 A1 | 9/2010 | Liu et al. | |

FOREIGN PATENT DOCUMENTS

| | | |
|---|---|---|
| CN | 101284662 | 10/2008 |
| CN | 101294904 | 10/2008 |
| CN | 101493457 | 7/2009 |
| JP | 2009501904 | 1/2009 |
| JP | 2009144158 | 7/2009 |
| JP | 2009184907 | 8/2009 |
| TW | 200911685 | 3/2009 |
| TW | 200938481 | 9/2009 |
| WO | WO2005114298 | 12/2005 |

OTHER PUBLICATIONS

Chen Yi-Chieh et al, Single-Walled Carbon Nanotube Networks Decorated with Silver Nanoparticles: A Novel Graded SERS Substrate, J.Phys.Chem.C 2007, vol. 111, No. 44, pp. 16167-16173.

Zhang et al. Superaligned carbon nanotube grid for high resolution transmission electron microscopy of nanomaterials, Nano Letters, 2008, 8(8), pp. 2564-2569.

Tsai et al. "Electrochemical deposition of silver nanoparticles in multiwalled carbon nanotube-alumina-coated silica for surface-enhanced Raman scattering-active substrates", Electrochemistry Communications, 2009, 11, pp. 542-545.

* cited by examiner

SURFACE-ENHANCED RAMAN SCATTERING SUBSTRATE AND RAMAN DETECTING SYSTEM HAVING THE SAME

CROSS-REFERENCE

This application claims all benefits accruing under 35 U.S.C. §119 from China Patent Application No. 200910190213.4, filed on Sep. 15, 2009 in the China Intellectual Property Office, the disclosure of which is herein by reference. This application is related to copending applications entitled, "RAMAN DETECTING SYSTEM AND METHOD FOR USING THE SAME", filed Jun. 15, 2010 Ser. No. 12/815,545.

BACKGROUND

1. Technical Field

The present disclosure generally relates to SERS (surface-enhanced Raman scattering) substrates, particularly, an SERS substrate based on carbon nanotubes, and a Raman detecting system having the same.

2. Description of Related Art

Fabrication of a stable SERS substrate with high enhancement has been a focus because it is a precondition for the study of SERS effect. A typical SERS substrate is usually composed of rough metal surface or coupled metal particles. In a paper entitled, "Electrochemical deposition of silver nano-particles in multi-walled carbon nanotube-alumina-coated silica for surface-enhanced Raman scattering-active substrates," by Tsai Yu Chen et al, Electrochemistry Communications, 2009, 11, 542-545, an SERS substrate based on carbon nanotubes was proposed. The SERS substrate can be fabricated by means of a wet-state process and depositing Ag particles on a multi-walled carbon nanotube (MWCNT) alumina-coated silica film. However, the wet-state dispersion of carbon nanotubes includes chemical treatments, which usually leads to some defects and low usage of carbon nanotubes.

What is needed therefore is a stable and cost-effective SERS substrate based on carbon nanotubes.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILS DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
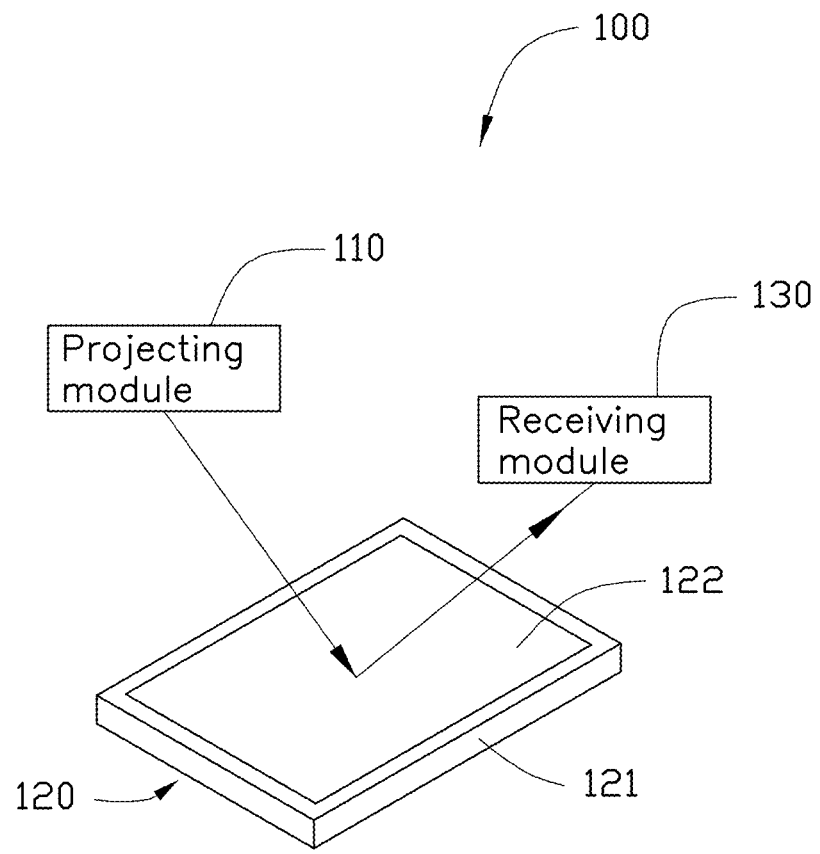
FIG. 1 is a schematic structural view of one embodiment of a Raman detecting system.

Referring to FIG. 1 of an embodiment, a Raman detecting system 100 includes a projecting module 110, a surface-enhanced Raman scattering (SERS) substrate 120, and a receiving module 130.

The projecting module 110 is configured to project a beam of light to the SERS substrate 120 to form a scattering light. Acreage of a cross section of the beam of light on the SERS substrate 120 can be less than or equal to 2 square millimeters. The projecting module 110 can include a light source such as argon laser. The light source can have a narrower frequency width. The beam of light can have a wavelength of about 450.0 nanometers to about 514.5 nanometers. In one embodiment, the wavelength of the beam of light is about 514.5 nanometers. More scattering light can be obtained by the beam of light with the wavelength of about 514.5 nanometers.

The receiving module 130 is configured to collect the scattering light scattered by the SERS substrate 120 to form a Raman spectra figure of a sample adhered on the SERS substrate 120. The receiving module 130 can include a multi-channel photon detector such as a charge coupled device (CCD), or a single-channel photon detector such as a photo-multiplier. Details of vibration modes of the sample can be read from the Raman spectra figure formed by the receiving module 130.

The SERS substrate 120 is configured to load the sample. The sample can be directly adhered to the SERS substrate 120. The sample can be a solid sample or a liquid sample. The solid sample can be sample powders, or particles adhering sample thereon. The liquid sample can be drops dissolving the sample therein, or molten sample. When the SERS substrate 120 is irradiated by the beam of light, a part of the beam of light can strike the sample to form the scattering light. Specifically, some photons of the beam of light can strike the sample and collide with molecules of the sample, thus, the momentum or the frequency of the photons can be changed. The variation of the frequency of the photons can correspond to variation frequencies of chemical bonds in the molecules of the sample. Thus, the molecular structure can be read from the scattering light.

The SERS substrate 120 can include a supporting element 121 and a carbon nanotube composite film 122.

The supporting element 121 is configured to support or fix the carbon nanotube composite film 122. The supporting element 121 can be a transparent substrate such as a glass panel, a plastic substrate, or a framing element such as a grid framework. Thus, less beams of light can be reflected by the substrate to disturb the scattering light. If the supporting element 121 is a transparent substrate, the carbon nanotube composite film 122 can be disposed on a surface of the transparent substrate directly. If the supporting element 121 is a framing element, the carbon nanotube composite film 122 can be suspended on the framing element. The area of the suspended part of the carbon nanotube composite film 122 can be greater than the cross-sectional area of the beam of light on the SERS substrate 120.

The carbon nanotube composite film 122 can include a carbon nanotube film structure and a metallic film disposed on the carbon nanotube film structure. The carbon nanotube film structure is capable of forming a free-standing structure. The term "free-standing structure" can be defined as a structure that does not have to be supported by a substrate. For example, a free-standing structure can sustain the weight of itself when it is hoisted by a portion thereof without any significant damage to its structural integrity. The free-standing structure of the carbon nanotube film structure is realized by the carbon nanotubes joined by van der Waals attractive force. So, if the carbon nanotube film structure is placed between two separate supporters, a portion of the carbon nanotube film structure, not in contact with the two supporters, would be suspended between the two supporters and yet maintain film structural integrity. Simultaneously, the supporting element 121 is an optional structure and can be omitted, if the carbon nanotube film structure is a free-standing structure.

The carbon nanotube film structure includes a plurality of carbon nanotubes uniformly distributed therein, and joined by van der Waals attractive force therebetween. The carbon nanotubes in the carbon nanotube film structure can be orderly or disorderly arranged. The term 'disordered carbon nanotube film structure' includes, but is not limited to, a structure where the carbon nanotubes are arranged along many different directions, such that the number of carbon nanotubes arranged along each different direction can be almost the same (e.g. uniformly disordered), and/or entangled with each other. 'Ordered carbon nanotube film structure' includes, but is not limited to, a structure where the carbon nanotubes are arranged in a consistently systematic manner, e.g., the carbon nanotubes are arranged approximately along a same direction and or have two or more sections within each of which the carbon nanotubes are arranged approximately along a same direction (different sections can have different directions). The carbon nanotubes in the carbon nanotube film structure can be single-walled, double-walled, and/or multi-walled carbon nanotubes.

Macroscopically, the carbon nanotube film structure may have a substantially planar structure. The planar carbon nanotube structure can have a thickness of about 0.5 nanometers to about 100 microns. The carbon nanotube film structure includes a plurality of carbon nanotubes and defines a plurality of micropores having a size of about 1 nanometer to about 500 nanometers. The carbon nanotube film structure includes at least one carbon nanotube film, the at least one carbon nanotube film including a plurality of carbon nanotubes substantially parallel to a surface of the corresponding carbon nanotube film.

Figure 2:
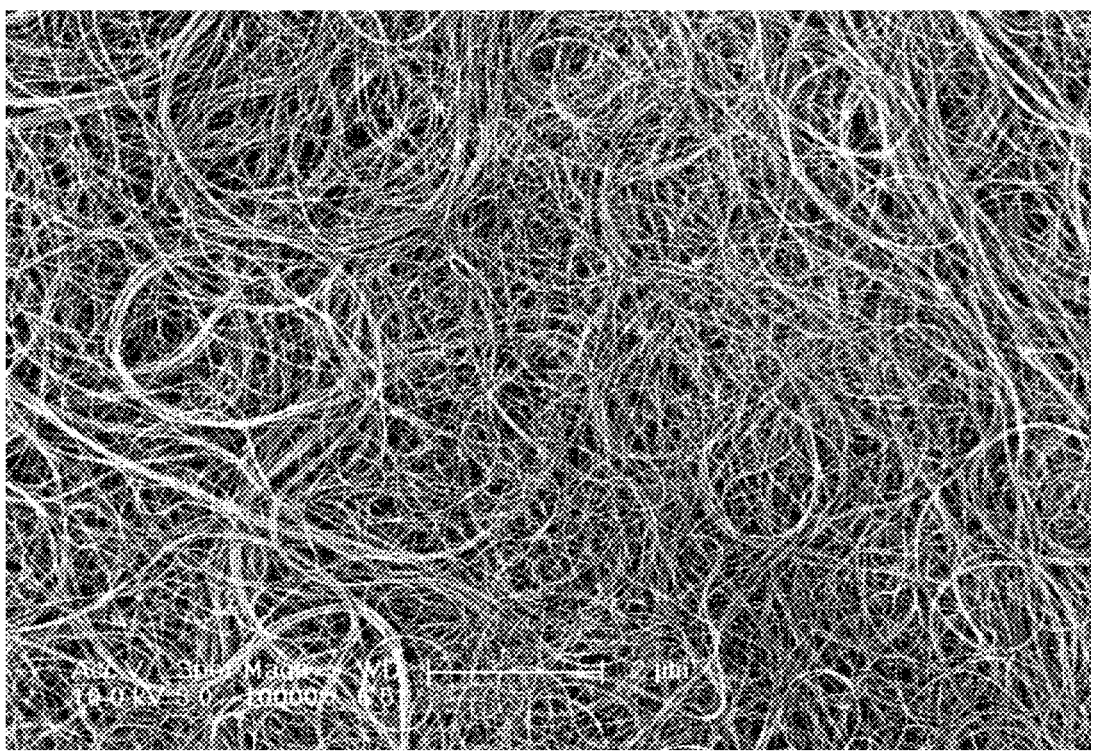
FIG. 2 shows a Scanning Electron Microscope (SEM) image of a flocculated carbon nanotube film.

The carbon nanotube film structure can include a flocculated carbon nanotube film as shown in FIG. 2. The flocculated carbon nanotube film can include a plurality of long, curved, disordered carbon nanotubes entangled with each other and can form a free-standing structure. Further, the flocculated carbon nanotube film can be isotropic. The carbon nanotubes can be substantially uniformly dispersed in the carbon nanotube film. The adjacent carbon nanotubes are acted upon by the van der Waals attractive force therebetween, thereby forming an entangled structure with micropores defined therein. Alternatively, the flocculated carbon nanotube film is very porous. Sizes of the micropores can be of about 1 nanometer to about 500 nanometers. Further, due to the carbon nanotubes in the carbon nanotube structure being entangled with each other, the carbon nanotube structure employing the flocculated carbon nanotube film has excellent durability, and can be fashioned into desired shapes with a low risk to the integrity of carbon nanotube structure. The flocculated carbon nanotube film, in some embodiments, will not require the use of structural support or due to the carbon nanotubes being entangled and adhered together by van der Waals attractive force therebetween. The flocculated carbon nanotube film can have a thickness of about 0.5 nanometers to about 100 microns.

Figure 3:
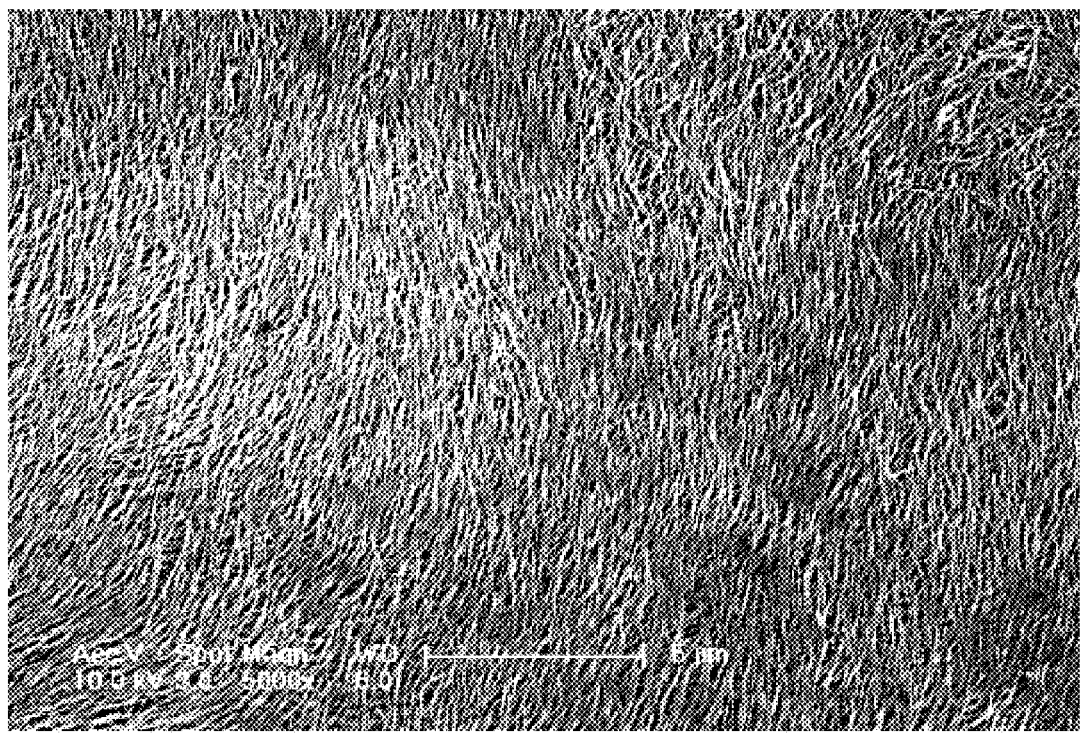
FIG. 3 shows an SEM image of a pressed carbon nanotube film.

The carbon nanotube film structure can include a pressed carbon nanotube film. The carbon nanotubes in the pressed carbon nanotube film can be arranged along a same direction or arranged along different directions. The carbon nanotubes in the pressed carbon nanotube film can rest upon each other. The adjacent carbon nanotubes are combined and attracted to each other by van der Waals attractive force, and can form a free-standing structure. An angle between a primary alignment direction of the carbon nanotubes and a surface of the pressed carbon nanotube film can be in an approximate range from 0 degrees to approximately 15 degrees. The pressed carbon nanotube film can be formed by pressing a carbon nanotube array. The angle is closely related to pressure applied to the carbon nanotube array. The greater the pressure, the smaller the angle. The carbon nanotubes in the carbon nanotube film can be substantially parallel to the surface of the carbon nanotube film when the angle is 0 degrees. A length and a width of the carbon nanotube film can be set as desired. The pressed carbon nanotube film can include a plurality of carbon nanotubes substantially aligned along one or more directions. The pressed carbon nanotube film can be obtained by pressing the carbon nanotube array with a pressure head. Alternatively, the shape of the pressure head and the pressing direction can determine the direction of the carbon nanotubes arranged therein. Specifically, in one embodiment, when a planar pressure head is used to press the carbon nanotube array along the direction perpendicular to a substrate. A plurality of carbon nanotubes pressed by the planar pressure head may be sloped in many directions. In another embodiment, as shown in FIG. 3, when a roller-shaped pressure head is used to press the carbon nanotube array along a certain direction, the pressed carbon nanotube film having a plurality of carbon nanotubes substantially aligned along the certain direction can be obtained. In another embodiment, when the roller-shaped pressure head is used to press the carbon nanotube array along different directions, the pressed carbon nanotube film having a plurality of carbon nanotubes substantially aligned along different directions can be obtained. The pressed carbon nanotube film can have a thickness of about 0.5 nanometers to about 100 microns, and can define a plurality of micropores having a diameter of about 1 nanometer to about 500 nanometers.

Figure 4:
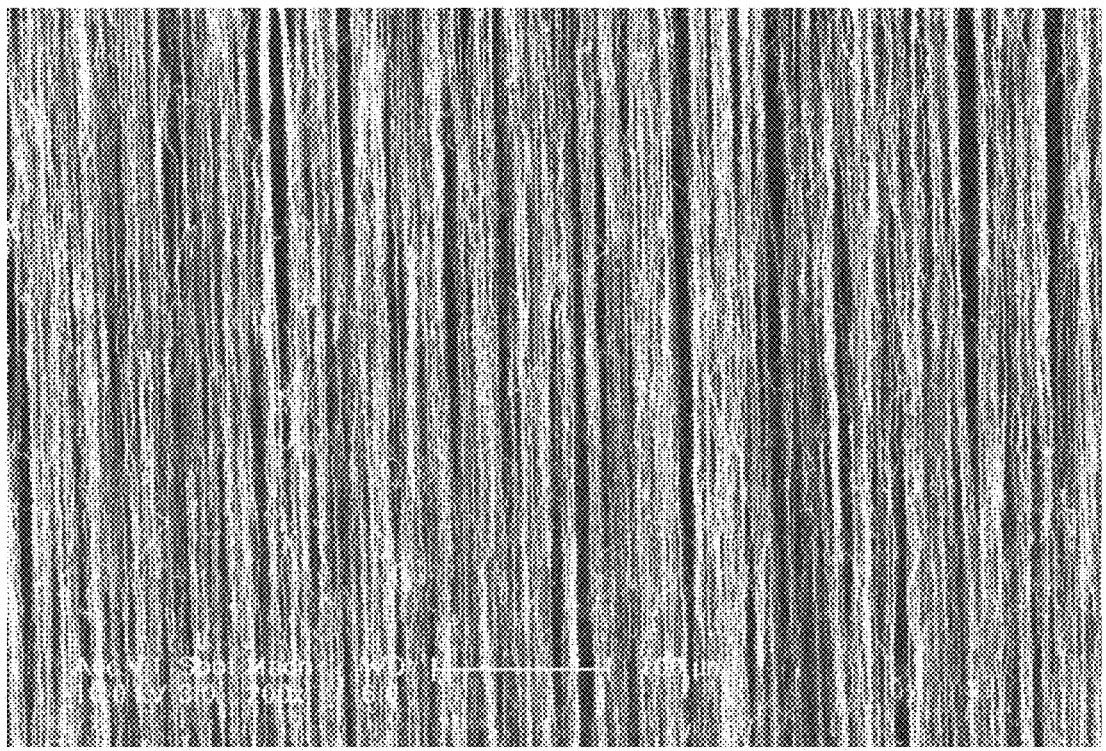
FIG. 4 shows an SEM image of a drawn carbon nanotube film.

In some embodiments, the carbon nanotube film structure includes at least one drawn carbon nanotube film as shown in FIG. 4. The drawn carbon nanotube film can have a thickness of about 0.5 nanometers to about 100 microns. The drawn carbon nanotube film includes a plurality of carbon nanotubes that can be arranged substantially parallel to a surface of the drawn carbon nanotube film. A plurality of micropores having a size of about 1 nanometer to about 500 nanometers can be defined by the carbon nanotubes. A large number of the carbon nanotubes in the drawn carbon nanotube film can be oriented along a preferred orientation, meaning that a large number of the carbon nanotubes in the drawn carbon nanotube film are arranged substantially along the same direction. An end of one carbon nanotube is joined to another end of an adjacent carbon nanotube arranged substantially along the same direction, by van der Waals attractive force. More specifically, the drawn carbon nanotube film includes a plurality of successively oriented carbon nanotube segments joined end-to-end by van der Waals attractive force therebetween. Each carbon nanotube segment includes a plurality of carbon nanotubes substantially parallel to each other, and joined by van der Waals attractive force therebetween. The carbon nanotube segments can vary in width, thickness, uniformity and shape. A small number of the carbon nanotubes are randomly arranged in the drawn carbon nanotube film, and has a small if not negligible effect on the larger number of the carbon nanotubes in the drawn carbon nanotube film arranged substantially along the same direction. The carbon nanotube film is capable of forming a free-standing structure. The term "free-standing structure" can be defined as a structure that does not have to be supported by a substrate. For example, a free-standing structure can sustain the weight of itself when it is hoisted by a portion thereof without any significant damage to its structural integrity. The free-standing structure of the drawn carbon nanotube film is realized by the successive segments joined end to end by van der Waals attractive force.

Understandably, some variation can occur in the orientation of the carbon nanotubes in the drawn carbon nanotube film as can be seen in FIG. 4. Microscopically, the carbon nanotubes oriented substantially along the same direction may not be perfectly aligned in a straight line, and some curve portions may exist. Furthermore, it can be understood that some carbon nanotubes are located substantially side by side and oriented along the same direction and in contact with each other.

Figure 5:
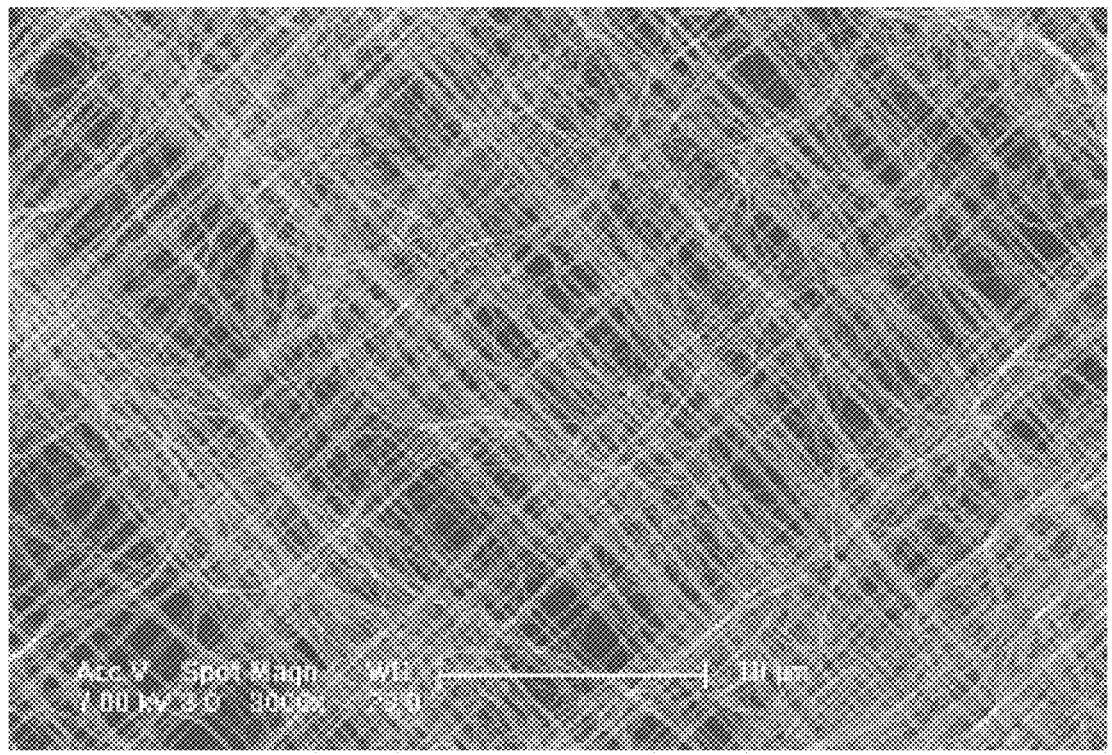
FIG. 5 shows an SEM image of a carbon nanotube film structure consisting of a plurality of stacked drawn carbon nanotube films defined as a CNT grid.

Referring to FIG. 5, in one embodiment, the carbon nanotube film structure of the SERS substrate 120 consists of a plurality of stacked drawn carbon nanotube films. The number of the layers of the drawn carbon nanotube films is not limited, provided the thickness of the carbon nanotube film structure can be maintained in a range from about 0.5 nanometers to about 100 microns. Adjacent drawn carbon nanotube films can be adhered by only the van der Waals attractive force therebetween. An angle can exist between the carbon nanotubes in adjacent drawn carbon nanotube films. The angle between the aligned directions of the adjacent drawn carbon nanotube films can range from 0 degrees to about 90 degrees. In one embodiment, the angle between the aligned directions of the adjacent drawn carbon nanotube films is substantially 90 degrees, thus a plurality of substantially uniform micropores is defined by the carbon nanotube film structure. If the sample adhered to the SERS substrate 120 is a liquid sample, a solvent film can be formed on the carbon nanotube film structure due to the substantially uniform micropores. The carbon nanotubes of adjacent drawn carbon nanotube films can overlap with each other to define a plurality of nodes therebetween capable of accommodating more samples therein.

The metallic film can be disposed on one surface of the carbon nanotube film structure or on two opposite surfaces of the carbon nanotube film structure. The metallic film can be formed by means of depositing a metallic material on the carbon nanotube film structure by, for example, e-beam evaporation or sputtering. A quartz crystal oscillator can be used to monitor the film thickness. A material of the metallic film can be noble metal or transition metal. The material of the metallic film can be gold, silver, copper, or nickel. The metallic film can have a thickness of about 1 nanometer to about 50 nanometers. In one embodiment, the metallic film has a thickness of about 18 nanometers to about 22 nanometers. In another embodiment, the metallic film with a thickness of about 3 nanometers to about 7 nanometers can improve the Raman enhancement factor of the SERS substrate 120. Microscopically, the metallic film can include a plurality of metallic particles. The metallic particles can be disposed on the outer surface of the carbon nanotubes of the carbon nanotube film structure. Simultaneously, more metallic particles can be disposed on the carbon nanotubes exposing out of the carbon nanotube film structure. The metallic particles each can have a diameter of about 1 nanometer to about 50 nanometers. A plurality of interparticle gaps can be formed among the metallic particles. The interparticle gap is about 1 nanometer to about 15 nanometers. In other words, gap or space between the metallic particles can be about 1 nanometer to about 15 nanometers. In one embodiment, the interparticle gap is about 2 nanometers to about 5 nanometers. Understandably, less than 1 percent of the metallic particles can have a diameter of about 50 nanometers. Less than 1 percent of the interparticle gap can be greater than 15 nanometers.

The carbon nanotubes of the SERS substrate 120 can have small dimensions and define a plurality of uniform micropores. Thus, the metallic particles having small size can be formed on the carbon nanotube film structure to define a plurality of interparticle gaps with a small size. The smaller the size of the interparticle gap, the greater the electromagnetic enhancement and Raman enhancement factor of the SERS substrate 120. A means for fabricating the SERS substrate 120 can be based on a technique of depositing the metallic particles on the carbon nanotube film structures formed by a dry-state process. Thus, a simple dry-state method can be used for fabricating low-cost, stable and sensitive SERS substrates 100.

The composite carbon nanotube film can further include a transition layer inserted between the carbon nanotube film structure and the metallic film. The transition layer can be deposited on the carbon nanotube film structure before the evaporation or sputtering of the metallic film. The transition layer can have a thickness of about 10 nanometers to about 100 nanometers. In one embodiment, the transition layer has a thickness of about 15 nanometers to about 30 nanometers. Microscopically, the transition layer can cover part or all the outer surfaces of the carbon nanotubes of the carbon nanotube film structure. The transition layer can provide a surface smoother than the surface of the carbon nanotube film structure. Stresses endured by the metallic particles in all orientations can be substantially equal to each other. Thus, the transition layer can improve the shape regularity of the metallic particles. The metallic particles can tend to form quasi-uniform spheres on the transition layer and improve electromagnetic enhancement and Raman enhancement factor of the SERS substrate 120. A material of the transition layer can be inorganic oxide such as silicon dioxide and magnesium oxide. In one embodiment, the transition layer is a silicon dioxide layer with a thickness of about 20 nanometers.

Figure 6:
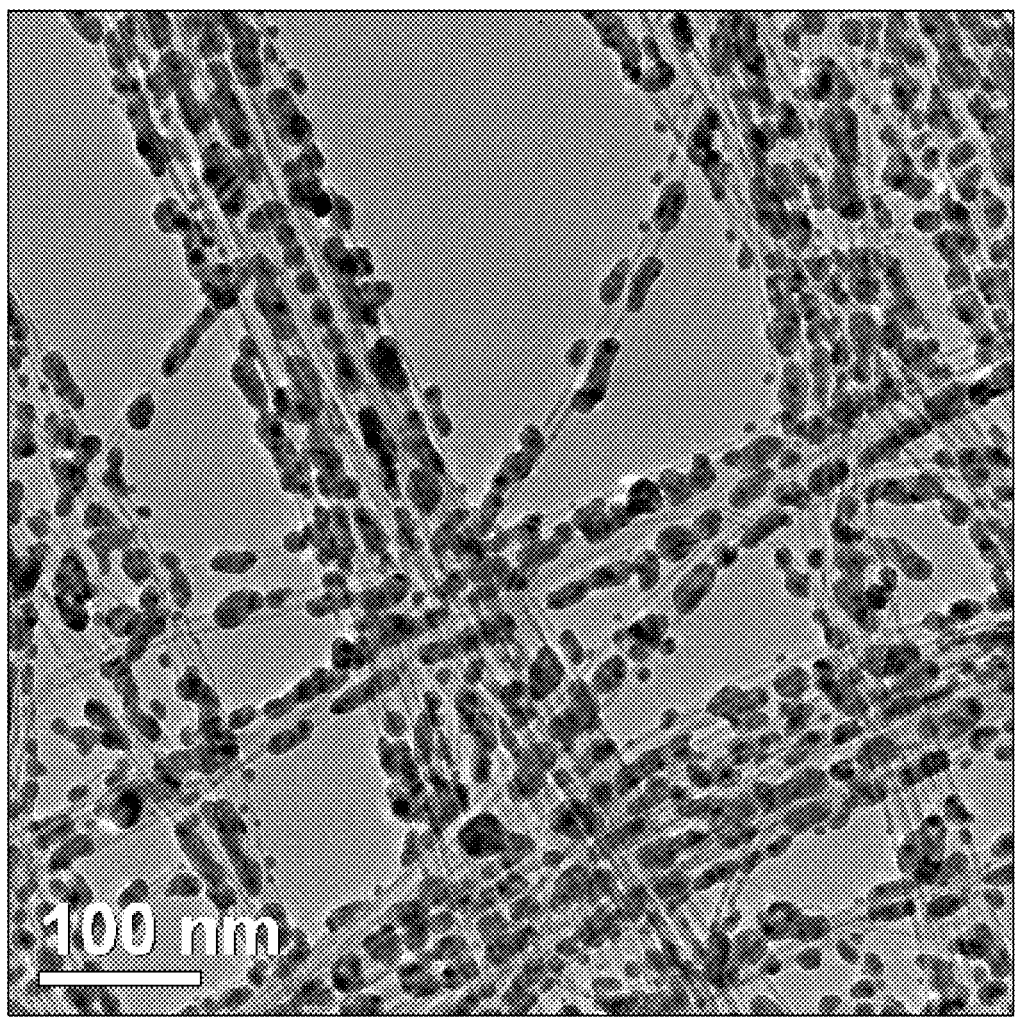
FIG. 6 shows a low magnification Transmission Electron Microscope (TEM) image of an SERS substrate defined as an Ag-CNT grid.
Figure 7:
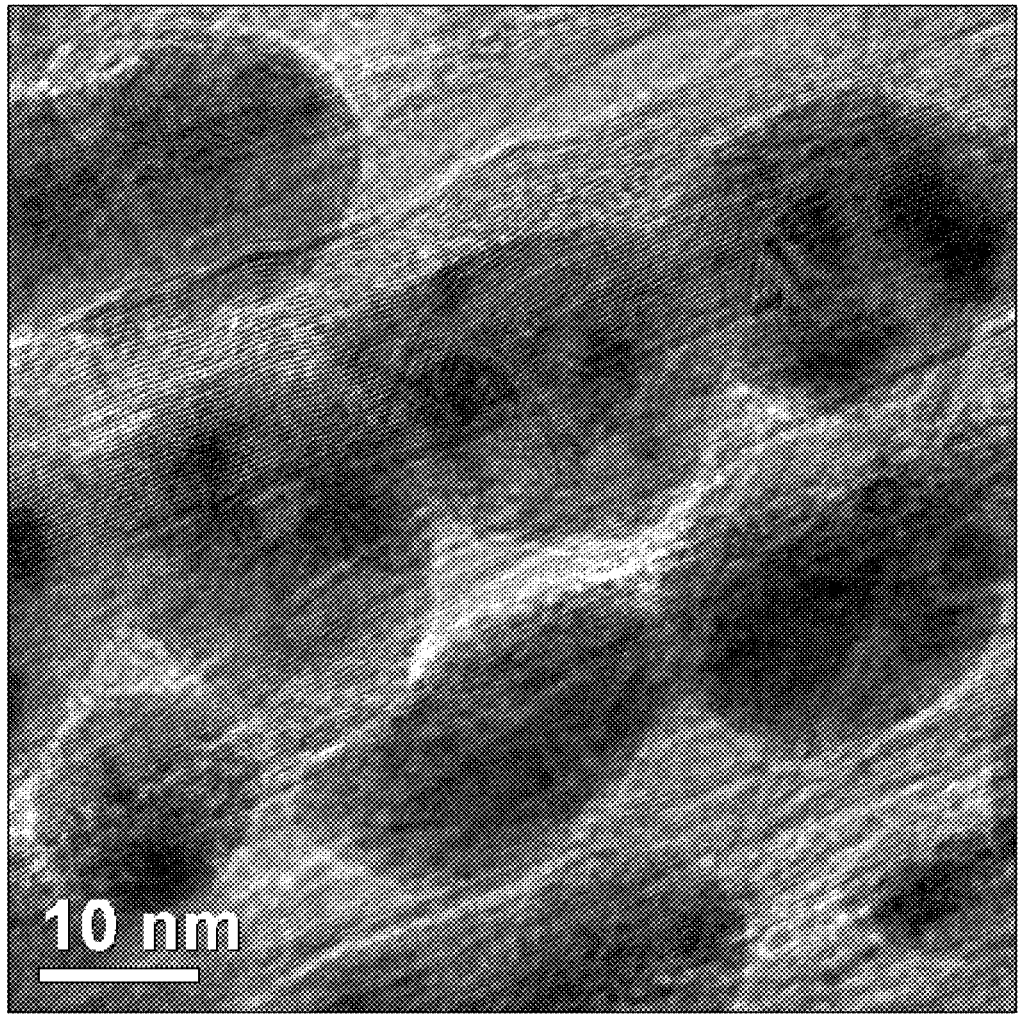
FIG. 7 shows a high magnification TEM image of the SERS substrate in FIG. 6.
Figure 8:
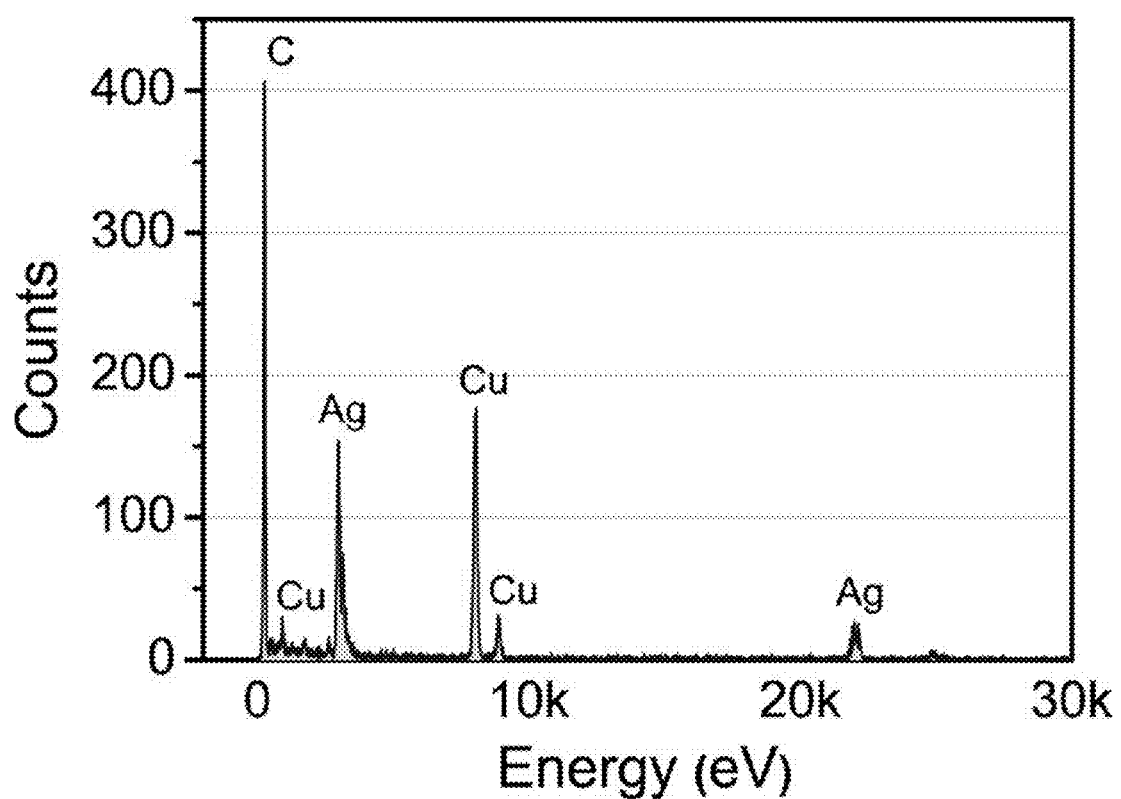
FIG. 8 shows an Energy Dispersive Spectrometer (EDS) image of the SERS substrate in FIG. 6.
Figure 9:
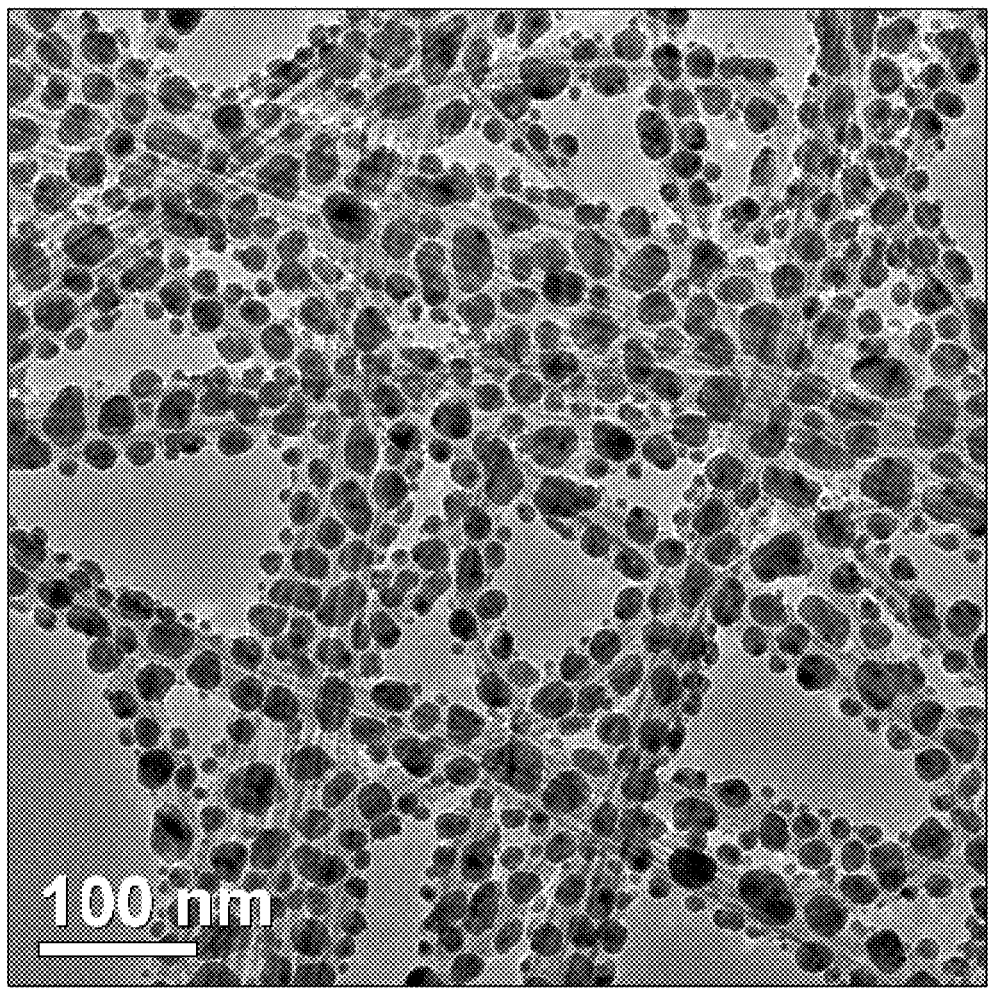
FIG. 9 shows a low magnification TEM image of an SERS substrate defined as an Ag—$SiO_2$-CNT grid.
Figure 10:
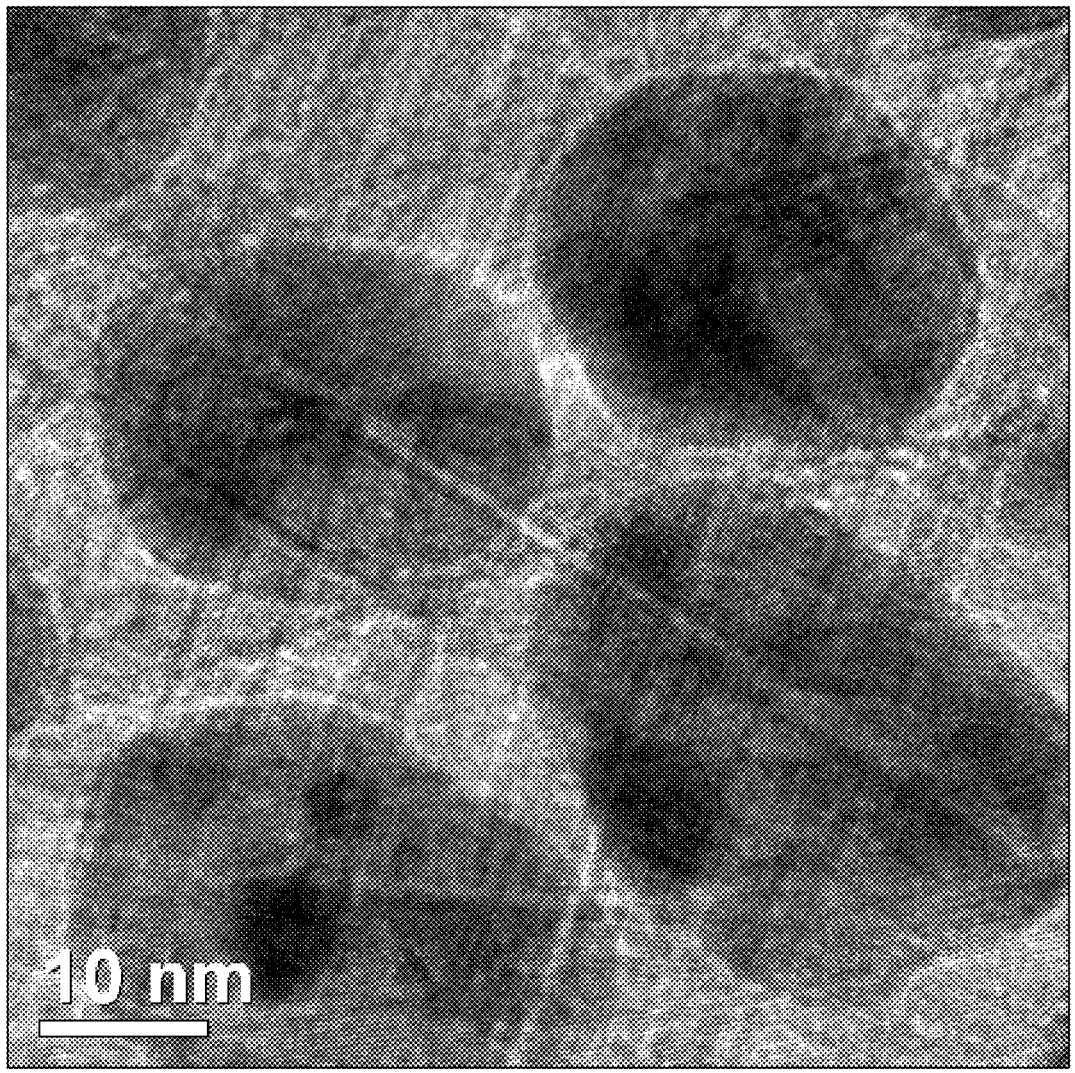
FIG. 10 shows a high magnification TEM image of the SERS substrate in FIG. 9.

The plurality of stacked drawn carbon nanotube films as shown in FIG. 5 can be defined as a CNT grid. Referring to FIG. 6 and FIG. 7, a SERS substrate 120 including the CNT grid and a silver film can be provided and be defined as an Ag-CNT grid. The silver film can be disposed on a surface of the CNT grid, and have a thickness of about 5 nanometers. An Energy Dispersive Spectrometer (EDS) image of the Ag-CNT grid can be shown in FIG. 8. In FIG. 8, the copper is from a TEM micro gird, thus, the elements of the Ag-CNT grid can consist of silver and carbon. Referring to FIG. 9 and FIG. 10, an SERS substrate 120 including the CNT grid, a silicon dioxide layer, and a silver film can be provided and be defined as an Ag—SiO$_2$-CNT grid. The silicon dioxide layer is deposited on the CNT grid and the silver film is deposited on the silicon dioxide layer. The silver film can have a thickness of about 5 nanometers. The silicon dioxide layer can have a thickness of about 20 nanometers.

Figure 11:
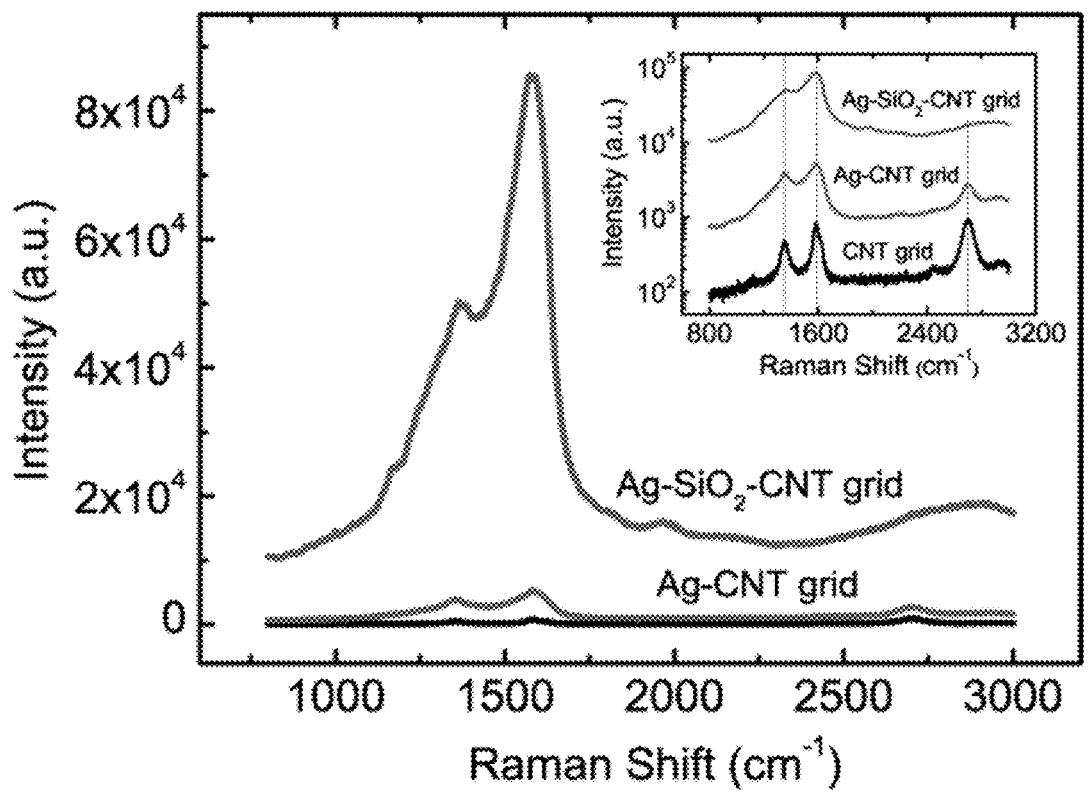
FIG. 11 shows a comparison of Raman spectra of the CNT grid, the Ag-CNT grid and the Ag—$SiO_2$-CNT grid.

To study and compare Raman spectra of the Ag-CNT grid and Ag—SiO$_2$-CNT grid without any sample thereon, three main Raman peaks of multi-wall carbon nanotubes (MWCNTs) can be measured, i.e., D peak (about 1350 cm$^{-1}$), G peak (about 1580 cm$^{-1}$) and 2D peak (about 2700 cm$^{-1}$) as shown in FIG. 11.

The Raman spectrum of the Ag-CNT grid can indicate that the silver nano-particles of the silver film can obviously enhance a Raman intensity of the MWCNTs. The Raman spectrum of Ag—SiO$_2$-CNT grid can indicate that the silicon dioxide inserted between the silver film and carbon nanotube film can further magnify the effect of enhancement of the SERS substrate 120. An intensity of G peak for the Ag-CNT grid and an intensity of G peak for the Ag—SiO$_2$-CNT grid can be enhanced by 6.5 and 104.8 times respectively as compared to an intensity of G peak of the CNT grid.

To test a Raman-enhancing capability of the CNT grid, the Ag-CNT grid, and the Ag—SiO$_2$-CNT grid, several organic molecules can be selected for measurement by the CNT grid, the Ag-CNT grid, and the Ag—SiO$_2$-CNT grid respectively.

Figure 12:
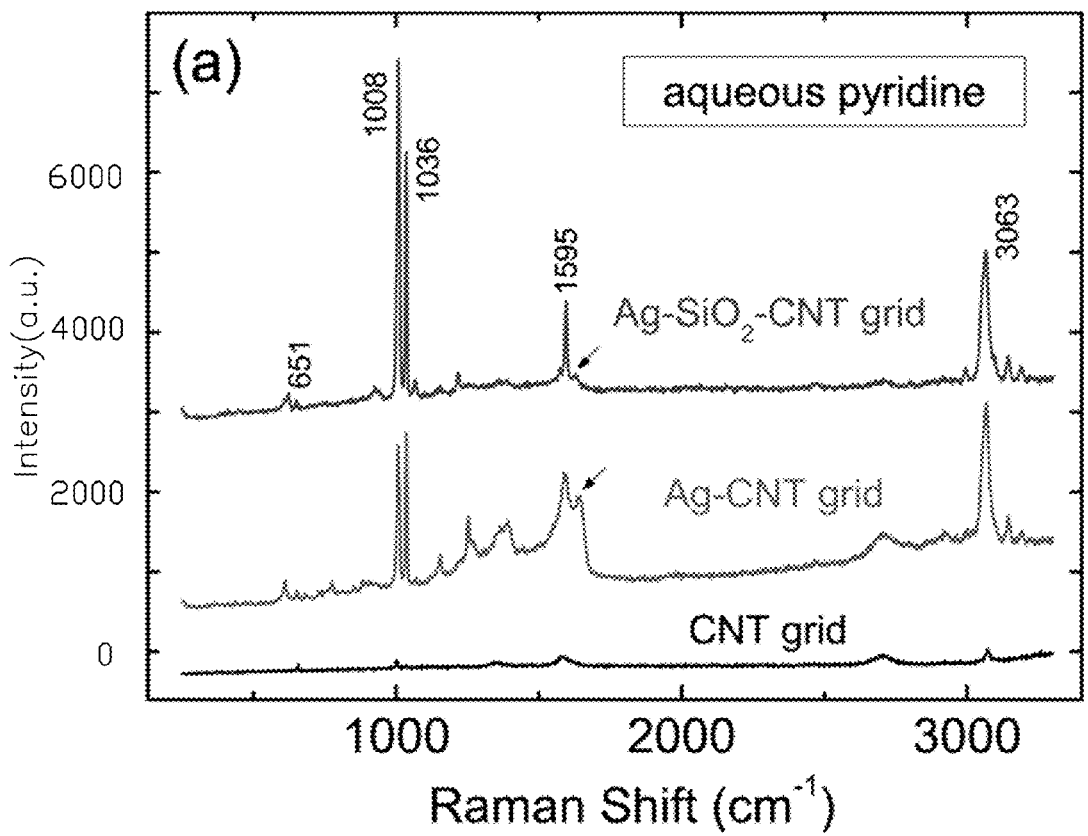
FIG. 12 shows a comparison of Raman spectra of aqueous pyridine on the CNT grid, the Ag-CNT grid, and the Ag—$SiO_2$-CNT grid.

A water solution of pyridine (volume ratio of pyridine to water=1:4) can be applied to the CNT grid and the Ag-CNT grid and the Ag—SiO$_2$-CNT grid respectively, and then Raman spectra of the CNT grid and the two substrates were recorded. As shown in FIG. 12, Raman spectrum of R6G on the CNT grid can not present the details of vibration modes of pyridine except several peaks at 657, 1002, 1034, and 3073 cm$^{-1}$ with very low intensity. In contrast, details and highly enhanced Raman peaks can be observed for pyridine adsorbed on the Ag-CNT grid and the Ag—SiO$_2$-CNT grid, and can display the capability of the Ag-CNT grid and the Ag—SiO$_2$-CNT.

Figure 13:
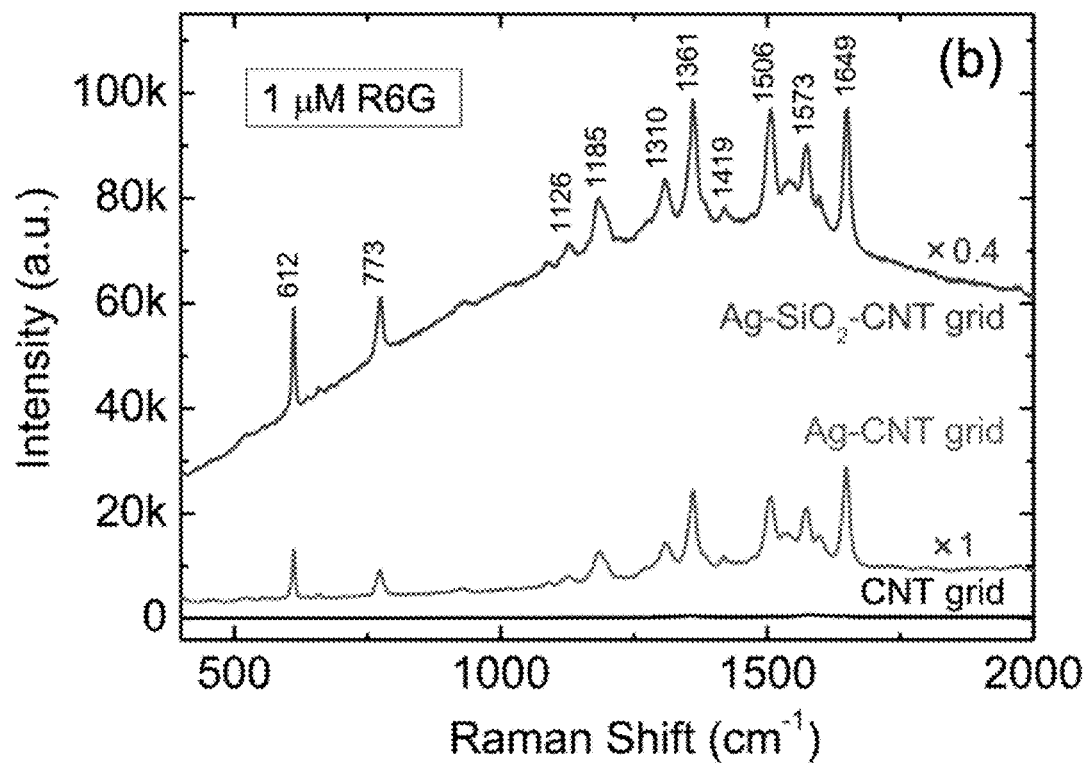
FIG. 13 shows comparison of Raman spectra of R6G on the CNT grid, the Ag-CNT grid, and the Ag—$SiO_2$-CNT grid.

A droplet of Rhodamine 6G (R6G) ethanol solution (10$^{-6}$ M) can be used to slightly soak the surfaces of the CNT grid, the Ag-CNT grid, and the Ag—SiO$_2$-CNT. Raman spectra of the CNT grid and the two substrates can be recorded after the evaporation of ethanol. As shown in FIG. 13, highly enhanced Raman peaks can be observed for R6G adsorbed on the Ag-CNT grid and the Ag—SiO$_2$-CNT grid, while Raman spectrum of R6G on the CNT grid cannot present any visible vibration modes of R6G. In normal Raman scattering, the fluorescence of R6G usually hinders the observation of its Raman signal because a cross section of Raman scattering is extremely smaller than a cross section of the fluorescence. In the Ag-CNT grid and the Ag—SiO$_2$-CNT grid, smaller interparticle gaps formed among the silver particles can improve the electromagnetic enhancement of the two substrates. Thus, both the cross section of the Raman scattering and the cross section of fluorescence can be increased. If the interparticle gap is small enough, the cross section of the Raman scattering can become comparable to or even larger than the cross section of the fluorescence. Therefore, obvious Raman peaks can be detected with the fluorescence spectrum. In experimental studies, a fluorescence quench of the R6G has often been observed because of a rapid energy transfer from excited electronic state to a surface of the metallic particles. In FIG. 13, the fluorescence of R6G is quenched to a low and steady state for the Ag-CNT grid, while the Raman signals on the Ag—SiO$_2$-CNT grid obviously superpose above a board fluorescence background. An effective way of charge transfer can be provided because of the silver film and the carbon nanotubes in Ag-CNT grid. The charge transfer can be helpful for the quench of R6G fluorescence. In contract, the silicon dioxide layer between the silver film and carbon nanotubes can evidently prevent the charge transfer, thus the quench of R6G fluorescence cannot be realized.

Figure 14:
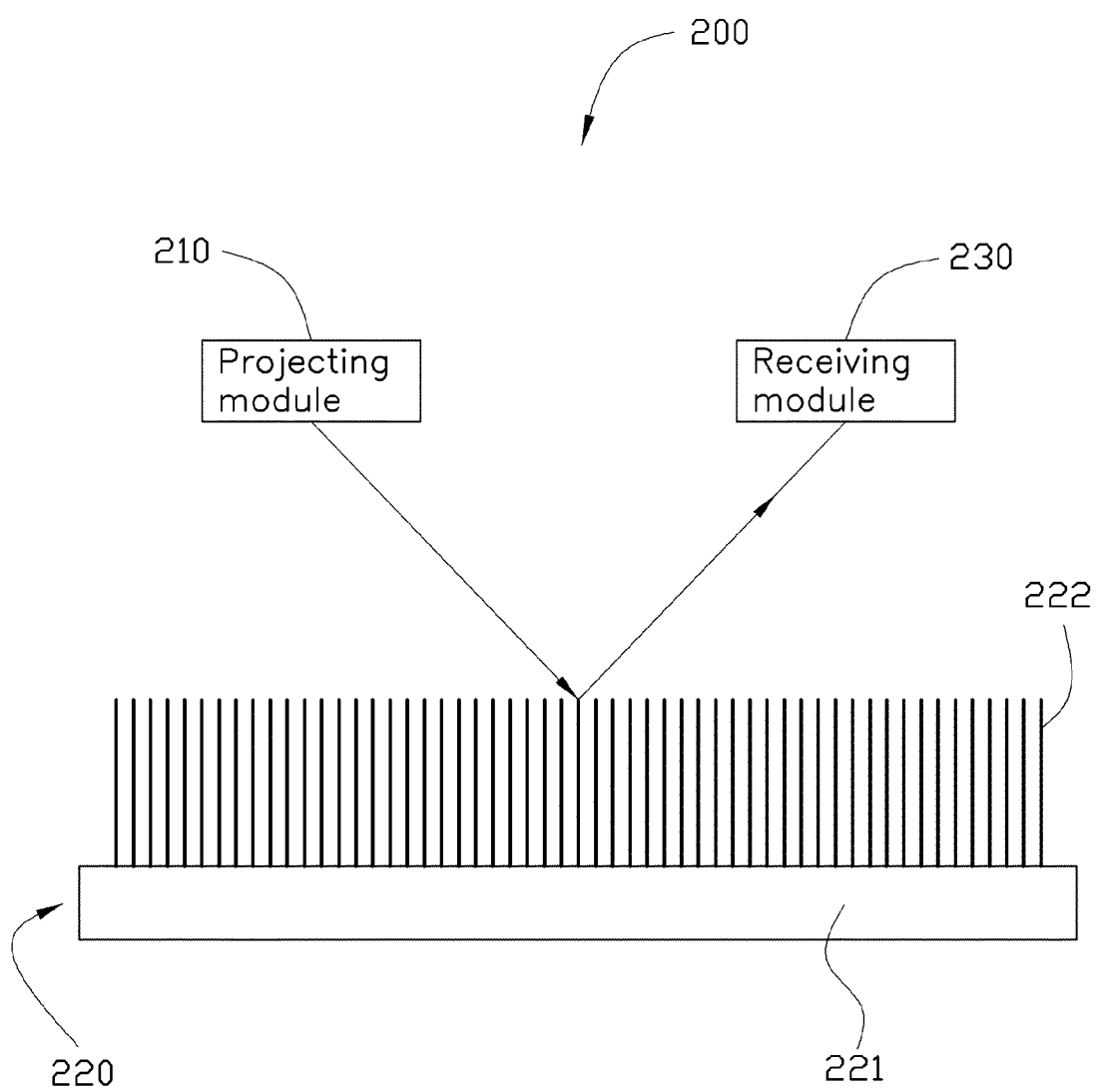
FIG. 14 is a schematic structural view of one embodiment of a Raman detecting system.

Referring to FIG. 14 of an embodiment, a Raman detecting system 200 includes a projecting module 210, an SERS substrate 220, and a receiving module 230. The projecting module 210 can be configured to project a beam of light to the SERS substrate 220 to form a scattering light. The SERS substrate 220 is configured to load the sample. The receiving module 230 is configured to collect the scattering light scatted by the SERS substrate 230 to form a Raman spectra figure.

Figure 15:
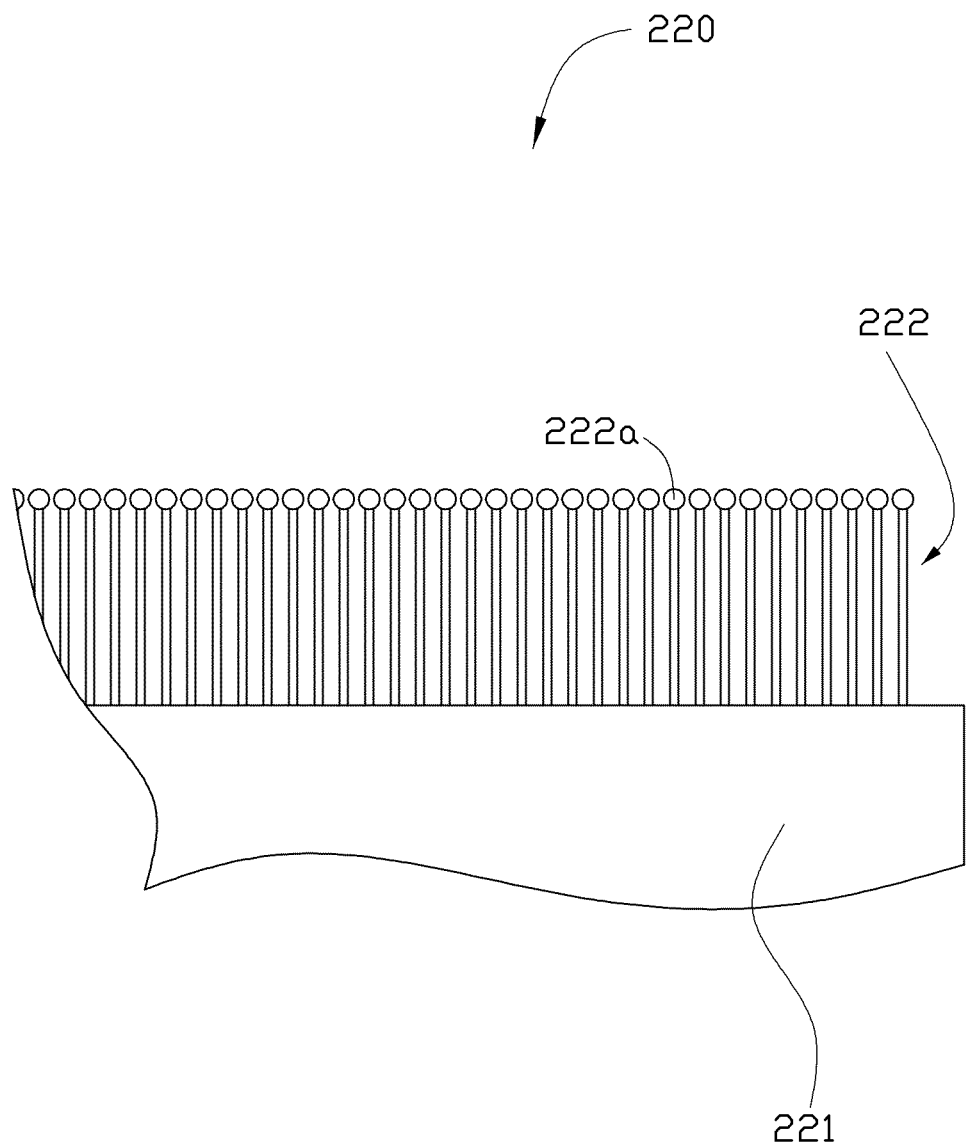
FIG. 15 is a schematic structural view of one embodiment of an SERS substrate.

Referring to FIG. 14 and FIG. 15, the SERS substrate 220 can include a supporting element 221 and a carbon nanotube composite film 222 supported by the supporting element 221. The supporting element 221 can be a transparent substrate such as a glass panel or a plastic substrate. The carbon nanotube composite film 222 can include a carbon nanotube film structure and a metallic film disposed on the carbon nanotube film structure. The carbon nanotube film structure can include a plurality of carbon nanotubes substantially perpendicular to a surface of the supporting element 221. The carbon nanotubes can be single-walled carbon nanotubes (SWCNTs), double-walled carbon nanotubes (DWCNTs), or multi-walled carbon nanotubes (MWCNTs). The carbon nanotubes of the carbon nanotube film are substantially parallel to each other and approximately perpendicular to the transparent substrate to form a super-aligned array. Heights of the carbon nanotubes can be substantially equal to each other. The carbon nanotubes in the super-aligned array are closely packed together by the van der Waals attractive force.

The compositions, features and functions of the Raman detecting system 200 in the embodiment shown in FIG. 14 are similar to the Raman detecting system 100 in the embodiment shown in FIG. 1. The difference is that the carbon nanotubes of the carbon nanotube film structure of the carbon nanotube composite film 222 are substantially perpendicular to a surface of the supporting element 221. The metallic film can be disposed on a surface of the carbon nanotube film structure opposite to the supporter element 221. Microscopically, the metallic film can include a plurality of metallic particles 222a. The metallic particle 222a can have a diameter of about 10 nanometers to about 50 nanometers. The metallic particles 222a can be disposed on distal ends of the carbon nanotubes as shown in FIG. 15.

Figure 16:
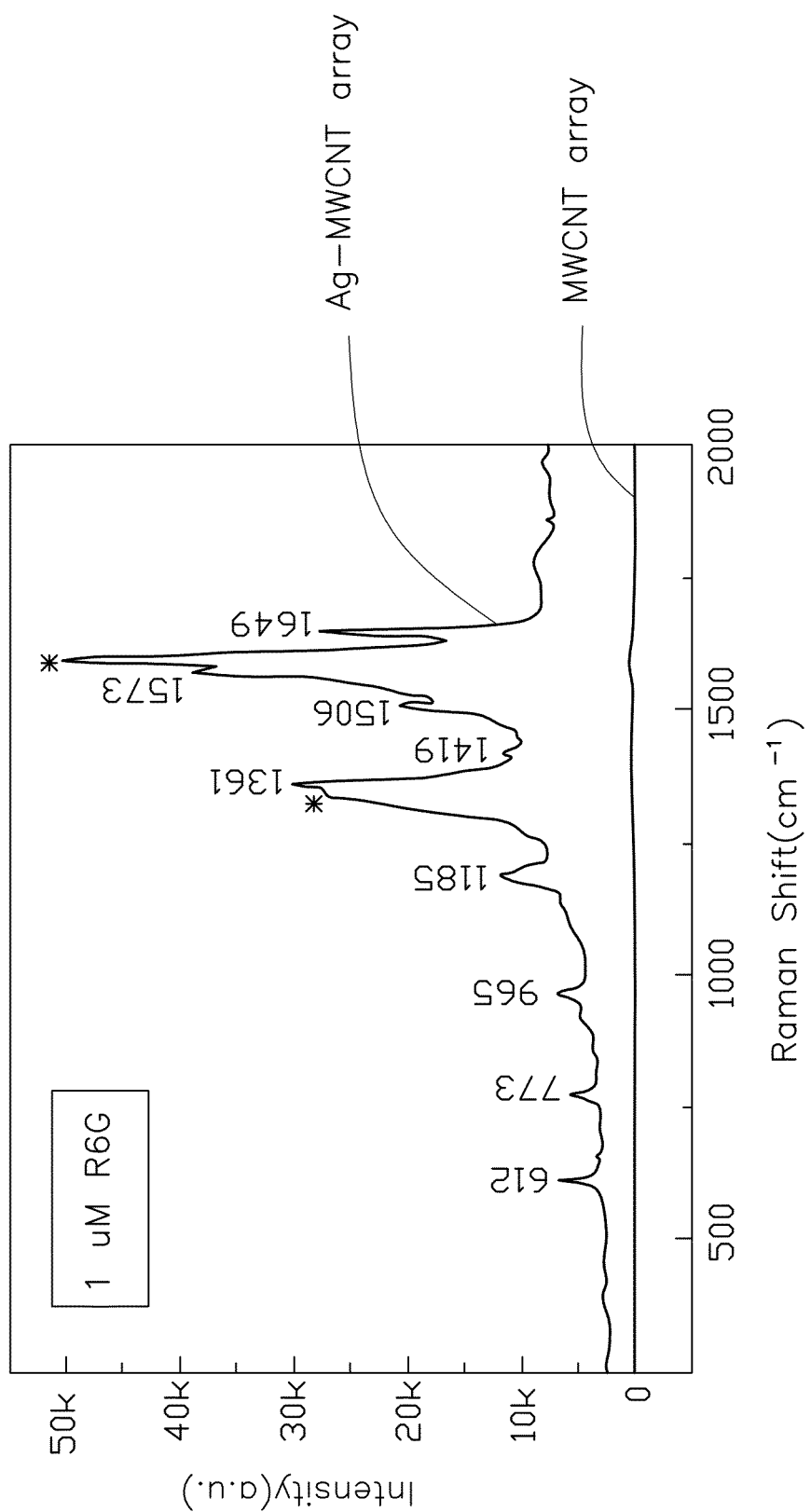
FIG. 16 shows a comparison of Raman spectra of R6G on an MWCNT array and an Ag-MWCNT array.

To test a Raman-enhancing capability of the SERS substrate 220 including the MWCNTs, an Ag-MWCNT array and a MWCNT array can be provided. The Ag-MWCNT array can include a carbon nanotube film structure consisting of MWCNTs and a silver film disposed on the carbon nanotube film structure. The silver film can have a thickness of about 13 nanometers to about 17 nanometers. The MWCNT array can include a carbon nanotube film structure consisting of MWCNTs. A droplet of R6G ethanol solution can be used to slightly soak the surfaces of the Ag-MWCNT array and the MWCNT array. As shown in FIG. 16, Raman spectrum for the MWCNT gird cannot present the details of vibration modes of Rhodamine 6G (R6G) with very low intensity. In contrast, details and highly enhanced Raman peaks can be observed for Rhodamine 6G adsorbed on the Ag-MWCNT array.

Figure 17:
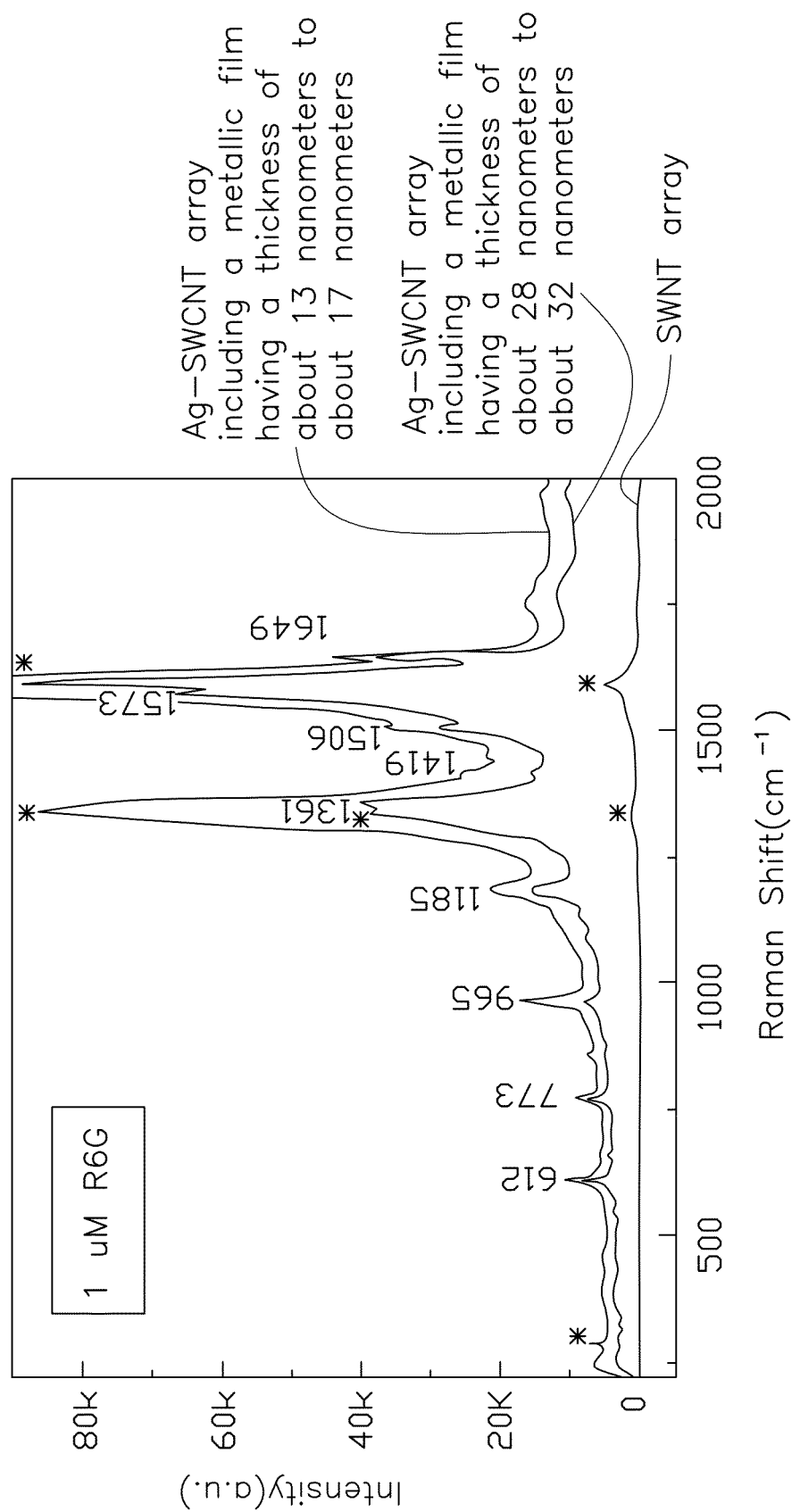
FIG. 17 shows a comparison of Raman spectra of R6G on an SWCNT array and two Ag-SWCNT arrays with different thicknesses of silver film.

To test a Raman-enhancing capability of the SERS substrate 220 including the SWCNTs, two Ag-SWCNT arrays and an SWCNT array can be provided. Each of the two Ag-SWCNT arrays can include a carbon nanotube film structure consisting of SWCNTs and a silver film disposed on the carbon nanotube film structure. The silver film of one Ag-SWCNT arrays can have a thickness of about 13 nanometers to about 17 nanometers. The silver film of the other one of the two Ag-SWCNT arrays can have a thickness of about 28 nanometers to about 32 nanometers. The SWCNT array can include a carbon nanotube film structure consisting of SWCNTs. A droplet of R6G ethanol solution can be used to slightly soak the surfaces of the two Ag-SWCNT arrays and the SWCNT array respectively. As shown in FIG. 17, Raman spectrum for the SWCNT gird cannot present the details of vibration modes of R6G with very low intensity. In contrast, details and highly enhanced Raman peaks can be observed for R6G adsorbed on two Ag-SWCNT arrays.

Finally, it is to be understood that the above-described embodiments are intended to illustrate rather than limit the disclosure. Variations may be made to the embodiments without departing from the spirit of the disclosure as claimed. Elements associated with any of the above embodiments are envisioned to be associated with any other embodiments. The above-described embodiments illustrate the scope of the disclosure but do not restrict the scope of the disclosure.

What is claimed is:

1. A surface-enhanced Raman scattering substrate, comprising:
   a carbon nanotube film structure comprising a plurality of carbon nanotubes joined by van der Waals attractive force therebetween and substantially aligned in a single direction; and
   a metallic layer comprising a plurality of metallic particles disposed on outer surfaces of the carbon nanotubes, wherein the carbon nanotube film structure further comprises transition layers disposed between the carbon nanotubes and the metallic particles, and the transition layers are made of silicon dioxide.

2. The substrate of claim 1, wherein the carbon nanotube film structure is a free-standing structure.

3. The substrate of claim 1, wherein the carbon nanotubes are substantially parallel to a surface of the carbon nanotube film structure.

4. The substrate of claim 3, wherein the carbon nanotubes are joined end to end by the van der Waals attractive force therebetween.

5. The substrate of claim 1, further comprising a plurality of stacked carbon nanotube film structures, wherein adjacent carbon nanotube film structures are adhered by the van der Waals attractive force therebetween.

6. The substrate of claim 1, further comprising a framing element, wherein a part of the carbon nanotube film structure is attached to the framing element, and another part of the carbon nanotube film structure is suspended.

7. The substrate of claim 1, wherein interparticle gaps are formed among the particles, each of the interparticle gaps is about 1 nanometer to about 15 nanometers.

8. The substrate of claim 7, wherein each of the interparticle gaps is about 2 nanometers to about 5 nanometers.

9. The substrate of claim 1, wherein each of the metallic particles has a diameter of about 1 nanometer to about 50 nanometers.

10. The substrate of claim 9, wherein the diameter of each of the metallic particles is about 18 nanometers to about 22 nanometers.

11. The substrate of claim 9, wherein the diameter of each of the metallic particles is about 3 nanometers to about 7 nanometers.

12. The substrate of claim 1, wherein the transition layer has a thickness of about 1 nanometer to about 50 nanometers.

13. The substrate of claim 12, wherein the thickness of the transition layer is about 3 nanometers to about 7 nanometers.

14. A surface-enhanced Raman scattering substrate, comprising:
   a carbon nanotube film structure;
   a transition layer disposed on a surface of the carbon nanotube film structure, wherein the transition layers are made of silicon dioxide; and
   a metallic layer disposed on a surface of the transition layer opposite to the carbon nanotube film structure, wherein the metallic layer has a thickness of about 3 nanometers to about 7 nanometers;
   wherein the carbon nanotube film structure comprises a plurality of carbon nanotube films, each of the carbon nanotube film comprises a plurality of carbon nanotubes substantially orienting along a preferred orientation and substantially parallel to a surface of the corresponding carbon nanotube film, and aligned directions of adjacent carbon nanotube films is substantially perpendicular to each other.

15. The substrate of claim 14, wherein the metallic layer consists of a plurality of metallic particles.

* * * * *